(12) United States Patent
Pocajt

(10) Patent No.: US 8,918,290 B2
(45) Date of Patent: Dec. 23, 2014

(54) METHOD AND SYSTEM TO IDENTIFY METAL ALLOYS

(75) Inventor: Viktor Pocajt, Belgrade (RS)

(73) Assignee: Key To Metals AG (CH)

(*) Notice: Subject to any disclaimer, the term of this patent is extended or adjusted under 35 U.S.C. 154(b) by 592 days.

(21) Appl. No.: 12/199,573

(22) Filed: Aug. 27, 2008

(65) Prior Publication Data

US 2009/0076739 A1    Mar. 19, 2009

Related U.S. Application Data

(60) Provisional application No. 60/968,212, filed on Aug. 27, 2007.

(51) Int. Cl.
  *G01N 31/00* (2006.01)
  *G01N 33/20* (2006.01)
(52) U.S. Cl.
  CPC ...................... *G01N 33/20* (2013.01)
  USPC ............................................... 702/28; 702/27
(58) Field of Classification Search
  CPC .................................. G01N 33/00; G06F 19/70
  USPC ........................................................ 702/27, 28
  See application file for complete search history.

(56) References Cited

U.S. PATENT DOCUMENTS

| | | | |
|---|---|---|---|
| 4,692,875 A * | 9/1987 | Riley et al. ...................... 702/27 |
| 5,062,127 A * | 10/1991 | Sayama et al. .................. 378/45 |
| 5,251,131 A * | 10/1993 | Masand et al. ..................... 704/9 |
| 7,416,524 B1 * | 8/2008 | Lobanov et al. .................. 506/8 |
| 2001/0022830 A1 * | 9/2001 | Sommer et al. ................. 378/45 |
| 2006/0074594 A1 * | 4/2006 | Ceder et al. .................... 702/182 |
| 2006/0217609 A1 * | 9/2006 | Diab et al. ..................... 600/336 |
| 2008/0033663 A1 * | 2/2008 | Brown et al. ................... 702/28 |
| 2009/0261848 A1 * | 10/2009 | Araki et al. .................... 324/705 |

FOREIGN PATENT DOCUMENTS

DE    10 2005 008844    *    9/2006

OTHER PUBLICATIONS

English Abstract of DE 10 2005 008844, Sep. 2006.*

* cited by examiner

*Primary Examiner* — Michael Nghiem
(74) *Attorney, Agent, or Firm* — Ostrolenk Faber LLP

(57) ABSTRACT

A method and system to identify an unknown metal alloy based on its chemical composition is provided in the present application. The chemical elements contained in the alloy are separated into key elements and trap elements. Then a similarity factor between a relative amount of each key element and a threshold value of said key elements is determined and a correlation factor is formed based on the similarity factors.

9 Claims, 9 Drawing Sheets

Smart Comp

Select similarity threshold: [0.85 ▾] — 5

Select standard: [All ▾]

Chemical Composition (%)

| Element | Value | Element | Value | Element | Value | Element | Value |
|---|---|---|---|---|---|---|---|
| ☑ C | 0.96 | ☑ Ni — 2 | 0.14 | ☑ W | 0.01 | ☐ B | |
| ☑ Si | 0.14 | ☑ Mo | 0.01 | ☐ Zr | | ☐ Bi | |
| ☑ Mn | 0.33 | ☑ Nb | 0.002 | ☐ Zn | | ☐ La | |
| ☑ P | 0.012 | ☑ Ti | 0.002 | ☐ As | | ☐ Se | |
| ☑ S | 0.015 | ☑ V | 0.004 | ☐ Sn | | ☐ Te | |
| ☐ Cu | | ☐ Ca | | ☐ Sb | | ☐ N | |
| ☑ Al | 0.001 | ☑ Pb | 0.004 | ☑ Ta | 0.01 | ☐ Fe | |
| ☑ Cr | 1.48 | ☑ Co | 0.005 | | | | |

[Submit] [Clear]

FIG. 1

| Smart Search | | Result(s) found 130 | |
|---|---|---|---|
| Material | Standard/Country | Subgroup | Similarity |
| S135 | B.S./United Kingdom | BS 2S135 | 0.94 |
| BL1 | B.S./United Kingdom | BS 4659 | 0.94 |
| EN31 | B.S./United Kingdom | BS 970 | 0.94 |
| 14100 | CSN/Czech Republic | CSN 41 4100 | 0.94 |
| 14109 | CSN/Czech Republic | CSN 41 4109 | 0.94 |
| 14209 | CSN/Czech Republic | CSN 41 4209 | 0.94 |
| Cr2 | GB/China | GB 1299 | 0.94 |
| GCr15 | GB/China | GB/T 3203 | 0.94 |
| GCr15SiMn | GB/China | GB/T 3203 | 0.94 |
| 12067 | WN/Germany | DIN 17350 | 0.94 |
| 13504 | WN/Germany | | 0.94 |

FIG. 2

Composition and CrossReference Table

Material: GCr15
Standard: G8
Country: China
Steel Group: Structural and constructional steel
Subgroup: GB/T 3203 Specification for carbonizing steels of bearings

Chemical Composition (%)

| Criteria | Min | Max | Approx |
|---|---|---|---|
| C | 0.9500 | 1.0500 | |
| Si | 0.1500 | 0.3500 | |
| Mn | 0.2500 | 0.4500 | |
| P | | 0.0250 | |
| S | | 0.0250 | |
| Cr | 1.4000 | 1.6500 | |
| Mo | | 0.0800 | |
| Ni | | 0.3000 | |
| Cu | | 0.2500 | |
| Ni-Cu | | 0.5000 | |

Cross-Reference Table

| Material | Standard / Country |
|---|---|
| 100 C 6 | AFNOR NF / France |
| 100 Cr 6 | AFNOR NF / France |
| 6 52100 | AISI / USA |
| 52100 | AS / Australia |
| SA-29 Grade E52100 | ASME / USA |
| A 295 52100 | ASTM / USA |
| A 519 ES2100 | ASTM / USA |
| A 7S2 Grade ES2100 | ASTM / USA |
| Ch | BOS / Bulgaria |
| SchCh 15 | BOS / Bulgaria |
| 14109 | CSN / Czech Republic |

FIG. 3

SmartCross

Numeral Designation: 1.4305

Material Designation: X 8 CrNIS 18.9

Standard: EN

Country: European Union

Steel Group: Stainless and heat resisting steels

Subgroup: EN 10088-1 Austenitic stainless steels

Comment: List of stainless steels

Select Similarity threshold: 0.70 v

Smart Search

Result(s) found 187

| Material | Standard / Country | Subgroup | Similarity |
|---|---|---|---|
| 1.4305 | DIN/Germany | DIN EN 10088-3 | 1.00 |
| 1.4305 | DIN/Germany | DIN 17440 | 1.00 |
| 1.4305 | DIN/Germany | | 1.00 |
| 1.4305 | DIN/Germany | DIN EN 10088-1 | 1.00 |
| 1.4305 | DIN/Germany | DIN 17440 | 1.00 |
| X8CrNIS 18-9 | DIN/Germany | DIN EN 10088-1 | 1.00 |
| X8CrNIS 18-9 | DIN/Germany | DIN 17440 | 1.00 |
| X 12CrNIS 18.9 | DIN/Germany | DIN 17440 | 1.00 |
| X 10CrNIS 18.9 | DIN/Germany | | 1.00 |
| X8 CrNIS 18.9 | E/European Union | EN 10088-1 | 1.00 |

FIG. 4

| Element | Weight | Thresh |
|---|---|---|
| Al | 1 | 0.02 |
| As | 1 | 0.03 |
| B | 1 | 0.0008 |
| Bi | 1 | 0.03 |
| C | 9 | 0.5 |
| Ca | 1 | 0.005 |
| Co | 1 | 0.3 |
| Cr | 6 | 0.15 |
| Cu | 1 | 0.1 |
| Fe | 1 | 0 |
| La | 1 | 0.03 |
| Mn | 3 | 0.4 |
| Mo | 2 | 0.05 |
| N | 1 | 0.01 |
| Nb | 1 | 0.015 |
| Ni | 3 | 0.15 |
| P | 1 | 0.01 |
| Pb | 1 | 0.1 |
| S | 1 | 0.01 |
| Sb | 1 | 0.001 |
| Se | 1 | 0.03 |

Weight group 2

Save weights

METHOD AND SYSTEM TO IDENTIFY METAL ALLOYS

CROSS-REFERENCE TO RELATED APPLICATIONS

The present application claims benefit of and priority to U.S. Provisional Patent Application No. 60/968,212 entitled METHOD TO IDENTIFY METAL ALLOYS filed Aug. 27, 2007, the entire contents of which are hereby specifically incorporated by reference herein.

BACKGROUND

1. Field of the Disclosure

The present disclosure lies in the field of identifying metals based on chemical or mechanical properties.

2. Related Art

In general, metal alloys are usually prepared to improve on the properties of their components. Metal alloys often are custom made and therefore have individual properties. For instance, steel is stronger than iron, its primary component. The physical properties of an alloy, such as density, reactivity and electrical and thermal conductivity may not differ greatly from the alloy's elements, but engineering properties, such as tensile strength, shear strength and Young's modulus, can be substantially different from those of the constituent materials. Therefore, it is important to be precisely aware of the properties of a material used in a certain engineering application, e.g. for bridges, buildings, ships or airplanes or other applications.

Although it is possible to determine by chemical and mechanical testing the composition and the physical and engineering properties of a metal alloy to a certain degree, it still is not possible to safely determine the material used. Sometimes it is not even possible to determine the original supplier. Known problems, which may occur, are the need to make a cross-reference and find an equivalent material worldwide; quick and accurate access to metal properties; understanding what is a foreign standard about; and need to search metals based on chemical or mechanical properties.

U.S. Pat. No. 5,062,127 was published in 1990 and is directed to a fluorescence X-ray spectrometry method and device for determining the type and quantity of metals elements in metal and metal alloy samples. An object to be analyzed is positioned so that an X-ray beam that will be generated will coincide with a measurement point on the surface of the object where it is desired that the analysis be carried out. Spectral analysis of the captured fluorescence X-ray radiation is then carried out wherein the intensity of selected peaks corresponding to target elements is determined, whereby the relative composition of selected elements can be calculated, thus providing selective quantitative analysis for target elements at the measurement point. The relative composition can be calculated by performing a computer analysis of the spectrum of the captured fluorescence X-ray radiation in which a fundamental parametric method is applied to the intensity values for peaks corresponding to each target element. A precise identification of an unknown metal is not possible.

German Patent Documanet DE102005008844 was published in September 2006 and is directed to a method for classifying data. The method involves obtaining available data from a database of a data set or an electronic catalog and providing or automatically determining characteristic criteria of the data. The data is automatically classified into category structures based on rules provided with the help of the criteria and the structures are held ready in an output memory. Analyses of data sets with the criteria are executed in the structures. However, the method is not applicable to identify unknown metal alloys.

Thus, it would be beneficial to provide a solution for the above mentioned problems and to provide a method to precisely identify unknown metal alloys.

SUMMARY

It is an object of the present disclosure to provide a method to precisely identify unknown metal alloys.

The present application relates to a method to classify and group metal alloys such that it becomes possible to precisely identify their identity based on their chemical composition and/or mechanical properties or partial information thereof. One embodiment relies on a set of methods, based on metallurgical expertise and improved fuzzy rules, for classifying, searching and comparing of chemical and/or mechanical properties of metals.

A method of identifying an unknown metal alloy in accordance with an embodiment of the present application includes determining a chemical composition of the metal alloy, determining key elements and trap elements based on information retrieved from a database, comparing a relative amount of each key element present with threshold values of said key element retrieved from a dataset of a specific known metal alloy, determining a similarity factor between the relative amount of each key element and the threshold value of said key elements, forming a correlation factor based on the similarity factors, and providing a result list of metal alloys retrieved from the database having highest correlation factors.

A data processing system for identifying an unknown metal alloy in accordance with an embodiment of the present application includes a display and an operating system, wherein the operating system is operable to perform steps including determining a chemical composition of the metal alloy, determining key elements and trap elements based on information retrieved from a database, comparing a relative amount of each key element present with threshold values of said key element retrieved from a dataset of a specific known metal alloy, determining a similarity factor between the relative amount of each key element and the threshold value of said key elements, forming a correlation factor based on the similarity factors, and providing a result list of metal alloys retrieved from the database having highest correlation factors.

A computer readable medium in accordance with an embodiment of the present application has a computer executable program recorded thereon, wherein the computer executable program directs the computer to perform steps of identifying an unknown metal alloy including determining a chemical composition of the metal alloy, determining key elements and trap elements based on information retrieved from a database, comparing a relative amount of each key element present with threshold values of said key element retrieved from a dataset of a specific known metal alloy, determining a similarity factor between the relative amount of each key element and the threshold value of said key elements, forming a correlation factor based on the similarity factors, and providing a result list of metal alloys retrieved from the database having highest correlation factors.

A weighing factor may be applied to at least one specific key element to influence the relevancy of said specific key element in the calculation of the correlation factor based on the classification of the metal alloys. The correlation factor may be determined by a summation of the similarity factors.

Other features and advantages of the present application will become apparent from the following description of the invention which refers to the accompanying drawings.

BRIEF DESCRIPTION OF THE DRAWINGS

The herein described invention will be more fully understood from the detailed description of the given herein below and the accompanying drawings which should not be considered limiting to the invention described in the appended claims.

FIG. 1 illustrates a user interface for providing input data to the method in accordance with an embodiment of the present application;

FIG. 2 is a list of result sets provided by the method applied in accordance with an embodiment of the present application;

FIG. 3 is a result set in a detailed view in accordance with an embodiment of the present application;

FIG. 4 is a list of equivalent metal alloys in accordance with an embodiment of the present application;

DETAILED DESCRIPTION OF THE EMBODIMENTS

Figures 5, 6:
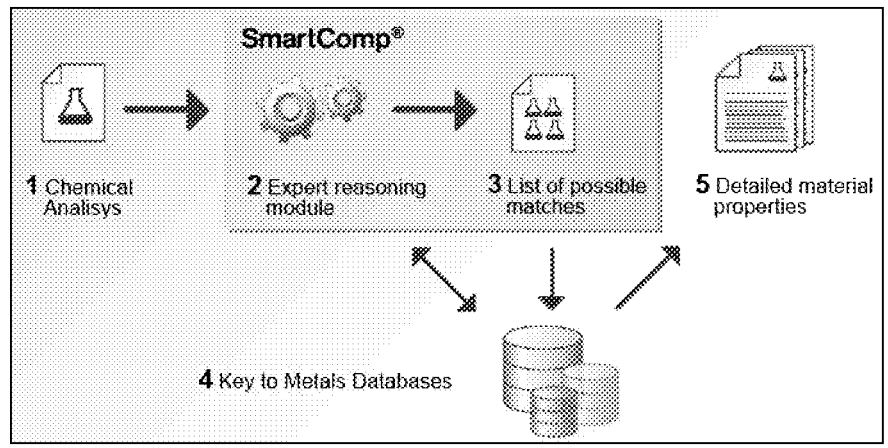
FIG. 5 illustrates the general setup of interaction between a method and a database in accordance with an embodiment of the present application.
FIG. 6 is a table with weight and threshold values.

A method according to the present application is suitable to search similar, respectively equivalent metals (herein expressions for metals and metal alloys are in general treated as equivalent) from a comprehensive database containing information about metals (e.g. like Key-to-Metals™) based on specific test results by comparing information about chemical compositions and/or mechanical properties, or partial information thereof. A method applied is designed to use a general pattern when comparing chemical compositions and properties of two metals remotely similar to the approach of a human expert. In contrast to a human expert, the disclosed method is more accurate and therefore reliable due to a standardized procedure which is based on measured values.

Depending on the field of application, the method may be applied to:

identify an unknown metal when its chemical analysis is known;

assessing conformity of tested metals with other standard- or proprietary metals;

finding unknown equivalents (cross-references) to the known metal;

Finding alloys that match testing results.

Thereby it becomes possible to improve engineering, R&D and design process, metal fabrication, metal processing and machining.

The method according to the present application in general may be subdivided in three different core parts which include different method steps:

(1) Identifying unknown metal by composition;

(2) Finding materials by mechanical properties testing results;

(3) Finding unknown equivalent materials.

Although their functionalities are different, the variations (1) and (2) can be combined with each other, as well as with algebra- or text based search, whilst (3) is foreseen preferably for standalone operation.

In general, a chemical composition of an unknown metal is determined, e.g. by a spectrometer or another technical device or in any other form, and made available directly or indirectly to an input device, e.g. a reading device or a specific form on a computer screen suitable to receive information (an example is shown in FIG. 1). If appropriate similarity threshold are adjusted and/or a particular standard of interest (e.g. DIN or Euronorm) is selected, then the method steps are applied to obtain a result list of grades (metal alloys), which match to the given composition. If appropriate, the results may be sorted according to a similarity factor (an example is shown in FIG. 2). Optionally, it is possible to retrieve detailed material properties and equivalents (see example as shown in FIG. 3). In an embodiment, a spectrometer to analyse materials is interconnected to a device to execute the method steps as described.

The principles and operation sequences of an embodiment of a method to identify metals will be described subsequently in more detail. After making available results of a chemical analysis of a metal, an expert reasoning module, which is based in one embodiment on a specific set of fuzzy rules of metallurgical expertise is initiated. This expert reasoning module is designed such that it is capable to distinguish specific important composition variations—which are related to key elements—from the noise and trap elements (Dummy Elements) based on data contained in a database and classifies the metal. Examples of key elements are e.g. C, Mg, Fe, Cr, Al. Examples of trap elements which are, in general, not of particular relevance for the alloy, are e.g. Cu.

A list of possible matches, if appropriate prioritized by similarity factors, is obtained through a comparison of relevant composition elements with a reference database. Good results may be obtained by using the database KEY to METALS™, for example, which comprises more than 100,000 alloys which are grouped and foreseen with a set of weighting factors suitable to be used in the rules applied. However, the method of the present application is not limited to use with this database. If appropriate, a user can e.g. review detailed metal properties through a hyperlink to the KEY to METALS™ database which comprises metal standards, chemical compositions, applications, mechanical properties of metallic alloys, special properties (e.g. fatigue data) and cross-reference tables.

Principles to classify metals according to the invention are described subsequently in more detail. In general, metals from a reference database are classified in a number of groups of metals, e.g. 20 to 30 (depending on the field of application other values may be appropriate), according to their metallurgical similarity and/or based on their chemical compositions. Examples of groups may include low-carbon low-alloyed steel, stainless steel, aluminum, brass, etc. In a preferred embodiment, the classification is manually pre-defined and it can be adapted without changing the basic method steps applied.

For each group of metals, a different set of weight and thresholds parameters for alloying elements is assigned (see example in FIG. 6). These weight and threshold parameters are used for calculating similarity of metals, whereby the weight parameter denotes relative importance of the alloying element, and the threshold parameter indicates at which level the element is considered in calculations. In a standard implementation of the method, weights and thresholds are fixed for each group of metals according to the absolute values related to the element in the database. In general, the weights cannot be altered by the user, but for some special implementations, e.g. with limited databases it may be important that a user can alter these values manually.

To establish a database suitable to be used in a method according to the present application, in general, the following method steps are preferred:
1. Provide a classification of metals based on metallurgical similarity and/or chemical composition and/or mechanical properties;
2. Retrieve data records of a multiplicity of metal alloys and classify the data records according to the classification;
3. Apply weight and threshold parameters for alloying elements;
4. Store the classification results in a database.

In an embodiment to retrieve information, the method applied investigates the data records of metals comprised within the database in a manually or automatically determined sequence, one by one or in parallel, determining their similarity with the chemical composition given, considering the weight factors. For example, for a selected metal alloy A from the reference database, the method estimates the similarity of the content of each element within its chemical composition to the content of the same element within the chemical analysis given. Similarity is defined as a degree of overlapping of the relative content (in %) of an element (e.g. carbon) in an certain alloy with the content of the same element (carbon in this example) in the analysis given. Degree of overlapping can normally go from 0 (no overlapping) to 1 (the amount measured fit into the carbon content defined for A). There is also a fuzzy part, when the content measured is relatively close to the boundaries defined in A, and consequently similarity level is close to 0 or 1. The similarity level is then calculated according to a trapeze rule, with a tolerance level that can be adjusted (see FIG. 7). For example, for a certain chemical element in a specific metal alloy the degree of overlapping is in a certain range defined as being 1 (exact). In a certain range adjacent to the range wherein the overlapping is defined as being 1 the degree of overlapping decreases linearly from 1 to 0 (no overlapping) with a certain declination. Depending on the field of application, other types of declination such as logarithmic or parabolic may be defined.

A similar fuzzy calculation may be applied to determine the composition boundaries within the database for the alloy A itself, since in most cases intervals for the alloying elements are not completely defined; only minimum or maximum values are given, but not both. Similarity level and composition boundaries as previously described can be calculated simultaneously, or composition boundaries can be pre-processed. The same comparison versus alloying elements in the reference alloy A is then repeated for all elements contained in the analysis, excluding the ones filtered out by thresholds. Total similarity factor between the analysis and the reference alloy A is calculated as a compound of similarities for individual elements, by applying weight factor for each alloying element. After determining similarity factor to the reference alloy A, the same procedure is repeated with all relevant materials within the database. The number of alloys that can be used is practically unlimited (e.g. in the database Key-to-Metals it is over 100.000). Result list contains all alloys with the similarity factors above user-defined similarity threshold. In the algorithm implementation, the other means of filtering and sorting results can be combined as well.

The herein described method can in a similar manner be applied in searching metals by results obtained from mechanical testing. This method in general includes the following method steps:
1. Provide mechanical testing results from an unknown metal, e.g. as obtained from measurement instruments, test results or documentation;
2. Input the provided testing results into a user interface;
3. If appropriate adjust similarity threshold and/or select a particular standard of interest (e.g. DIN or Euronorm);
4. Initiate an analysis process;
5. Obtain a result list of grades which match to the given composition, e.g. ordered by similarity factor.

If appropriate mechanical testing and chemical analysis can be combined. Thereby it becomes possible to identify materials in a combined mode.

In one embodiment, the method is implemented in a new release of a software with the name SmartMetals™. This software may include several sub-components as follows:
1) SmartComp™: Chemical analysis, with a goal of identifying unknown metal;
2) SmartMech™: Mechanical properties data obtained by testing or calculations;
3) SmartComp™: Known material, for which equivalents are searched.

Based on the method steps described above SmartMetals:
1) Classifies to which family of metal alloys an unknown alloy may belong;
2) Uses thresholds to filter out the measurement noise and to exclude irrelevant elements within the analysis
3) Applies set of pre-defined weights and fuzzy logic-based calculation to determine the level of similarity between the composition given and the composition of each of the metals in the database.

If only mechanical properties data obtained by testing or calculations are available, a modified algorithm is applied (SmartMech for example). In this case, there is no metal classification, since the composition is unknown, and there is a specific fuzzy-based calculation. The method is based on a comparison of mechanical properties of metals with information stored in form of data records within the database in an automatic sequence. Thereby one by one data record is compared, determining its similarity with mechanical properties provided by the interface. Similarity is defined in the same manner as described above as a degree of overlapping of the mechanical property in the alloy, e.g. tensile stress, with the user-inputted property value (tensile stress in this example) obtained by mechanical testing, calculation, or by other means. The degree of overlapping can reach from a value of 0 (no overlapping) to a value 1 (the amount measured fit into the tensile stress interval defined for A). If appropriate, there is a fuzzy part, when the property value inputted is relatively close to the boundaries defined in A, and consequently the similarity level is between 0 and 1. The similarity level is in this case also calculated according to the trapezes rule. Good results are obtained by applying fuzzy calculation to determine the mechanical properties boundaries within the database for the alloy itself, since in most cases the intervals for the properties are not completely defined: only minimum or maximum values are given, but not both.

Similarity level and mechanical properties boundaries described in previous paragraphs can be calculated simultaneously, or mechanical properties boundaries can be pre-processed.

In case of mechanical properties, there are, in general, no threshold values, since they have no physical meaning, and no pre-defined weights of the mechanical properties. Within the software implementation, an end-user may dynamically define weights, according to their relative importance for the particular application.

When searching by mechanical properties is applied combined with search by analysis, both versions of the algorithm are normally applied "as is" in a sequence, first search by analysis and then by properties or vice-versa.

The goal of cross-referencing, which is a common engineering activity, is to find equivalent metals to the selected one. Cross-referencing is mainly based on similarity of chemical compositions, and this is how it is done within SmartMetals, for example. Instead of having exact chemical composition as an input, composition of a metal alloy A, selected by the end-user, is available. Since this composition is in general defined by incomplete interval, fuzzy calculation pre-processing is applied to determine the composition boundaries within the alloy to be determined. After the composition of the alloy is determined (calculated), SmartMetals can classify to which group of metals it belongs, and apply thresholds and weight factors.

A SmartCross algorithm then continues with comparing the chemical composition of the alloy with
  all alloys within the database, or
  only the alloys belonging to the same group.

This choice can be implemented as user-defined. Comparison of compositions is being made by comparing the content of each element within A with its content within B, an other alloy in the database. Similarity is defined as a degree of overlapping of the content of an element (e.g. carbon) in A with the content of the same element (carbon in this example) in B. Degree of overlapping again goes from 0 (no overlapping) to 1 (the content is exactly the same). Compound similarity factor is calculated in the same way as described above. Result list fetches similar metals, as in the example on the FIG. 4.

A better understanding of the present application may be obtained by the further detailed description below which, when examined in connection the accompanying drawings, sets forth embodiments of the inventions described herein.

FIG. 1 shows an embodiment of a user interface to input data into a computer program to perform the methods steps according to an embodiment of the present application. The input data in the illustrated example relates to measured values resulting from a material test performed by a spectrometer (not shown in detail). The applied method (so called SmartMetals Algorithm) is embedded into the computer program, which is designed to precisely identify metals and metal alloys based on a chemical composition. Thereby it becomes possible to determine the chemical composition of an unknown metal alloy, as obtained by an interconnected measurement, and input them into a sample form as shown. If appropriate, it is possible to adjust a similarity threshold and/or select a particular standard of interest (e.g. DIN or Euronorm).

As can be seen, a choice of possibly contained chemical elements 2 is provided in an input form 1. The presence can be determined by check boxes 3 and data fields 4 suitable to receive information regarding the chemical composition. A threshold field 5 determines the sensibility of the method applied.

FIG. 2 shows example results retrieved by a method according to an embodiment of the present application in the form of an output form 10. In a first column 11, information about metal alloys/materials determined are displayed. In a second and third column 12, 13, further information regarding the standard and/or geographic are displayed. In a fourth column 14, a similarity value is displayed indicating the likelihood of the result record retrieved.

FIG. 3 shows an example of a composition and cross reference table wherein on the left hand side the chemical composition of a certain material is visible. On the right hand side alternative materials are visible in a cross-reference table. In a header arranged above the tables, general information such as name, standard, country of origin, group about the specific material is preferably displayed.

FIG. 4 shows a result list with equivalent materials, ordered by a similarity factor. After a specific material is selected, equivalents are found based on chemical composition comparison and classification. The results are displayed in a list of similar/equivalent materials, ordered by similarity factor. If appropriate, every result record may be hyperlinked to a reference data base to retrieve further information.

FIG. 5 shows in general terms an embodiment of the invention in operation. After entering results of a chemical analysis of a certain metal (1), an original expert reasoning module (2) determines based on the method described above, distinguishes important composition variations from the noise and trap elements and classifies the metal based on data records stored in a database (4) and provides a list of possible matches (3), prioritized by similarity factors (3) is then obtained through a comparison with the reference database, e.g. more than 100,000 alloys from the Key to Metals databases (4).

Detailed metal properties can be reviewed through a hyperlink from SmartComp to Key to Metals databases (5). Key to Metals databases include metal standards, chemical compositions, applications, mechanical properties of metallic alloys, special properties (e.g. fatigue data) and cross-reference tables.

FIG. 6 shows in a table, an example of weighting factors and threshold values for several chemical elements. For each group of metals, a different set of weight and thresholds parameters for alloying elements is assigned. These weight and threshold parameters are used for calculating similarity of metals, whereby the weight parameter denotes relative importance of the alloying element, and the threshold parameter indicates at which level the element is considered in calculations. In a standard implementation of the method, weights and thresholds are fixed for each group of metals according to the absolute values related to the element in the database. In general, the weights cannot be altered by a user, but for some special implementations, e.g. with limited databases it may be important that a user can alter these values manually.

Figure 7:
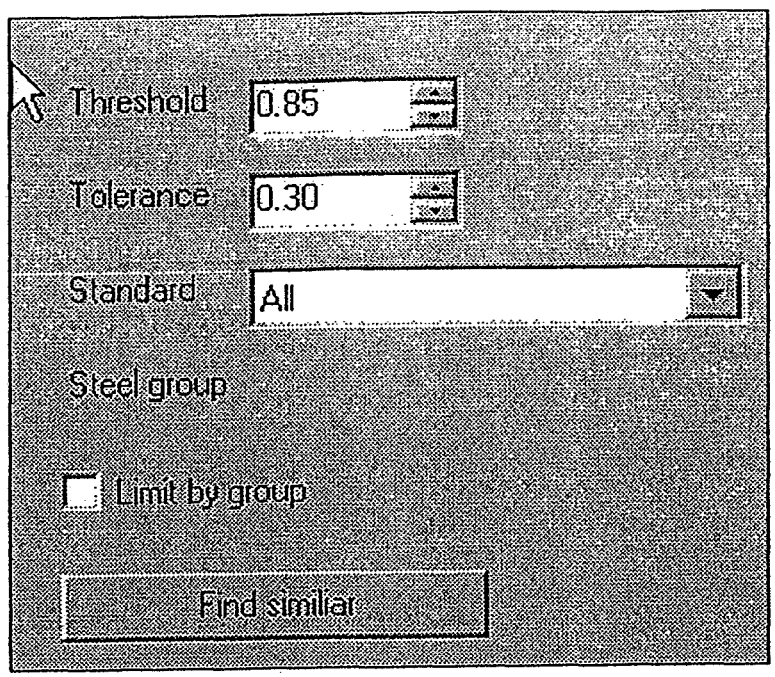
FIG. 7 illustrates an example how to set weight and threshold values in accordance with an embodiment of the present application.

FIG. 7 an example of an input form to enter a set of weights and thresholds. The similarity level may then calculated e.g. according to the trapezes rule, with a tolerance level that can be adjusted.

Figure 8:
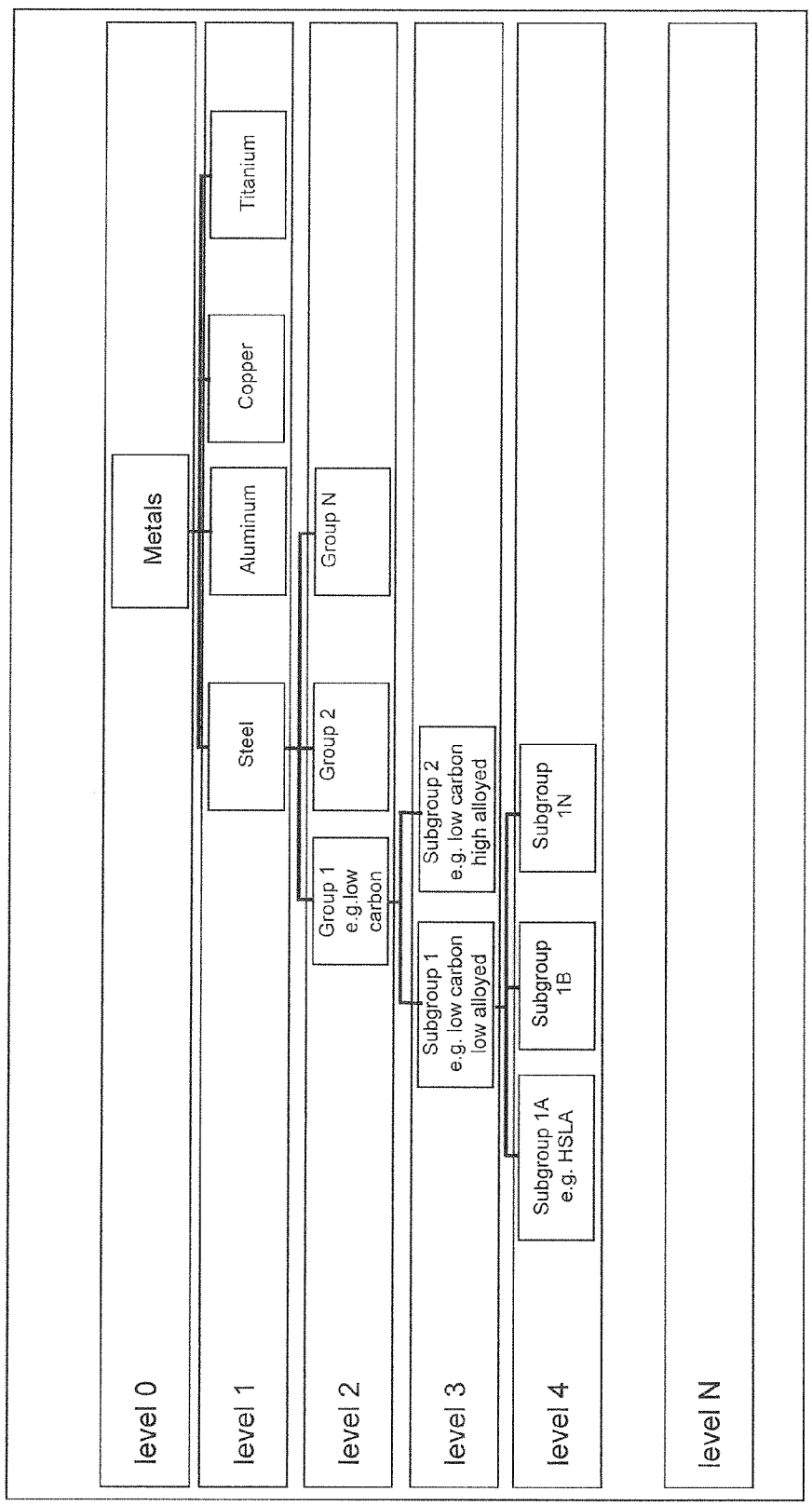
FIG. 8 is a diagram schematically indicating different levels of analyzing.

FIG. 8 shows in a schematic manner an organization of a database with several levels. The key and trap elements are group-dependent. This means that it might be relevant that a certain metal is analyzed based on different attempts, i.e. groups and subgroups and the results are then compared and the best result is evaluated.

Figure 9:
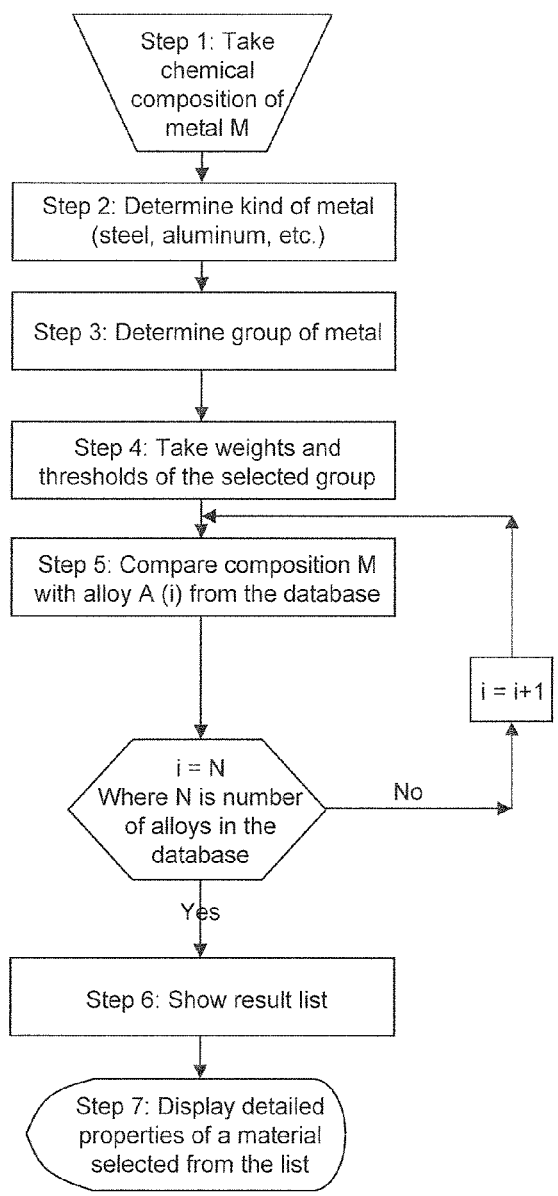
FIG. 9 is a flow chart with method steps in accordance with an embodiment of the present application.

FIG. 9 schematically indicates in flow chart of method steps to determine the composition and/or the mechanical properties of a metal alloy. In contrast to a human expert, the present method is based on the presence of trap and dummy elements and their qualification according to threshold-values. A human expert does not define weights and thresholds explicitly as numbers, but would qualify based on his experience which might lead to false results. In principle, a method according to the present application includes the following method steps: (1) Provide the chemical composition of a metal; (2) if appropriate, manually or automatically make a coarse classification of the metal based on its chemical nature (steel, aluminum, etc); (3) determined the group of metal based on the information available; (4) retrieve weights and thresholds of the determined group of metal from the database; (5) compare key elements of the metal with data sets from a database; (6) when results are found, show result list; (7) if appropriate show detailed properties of materials found.

Figure 10:
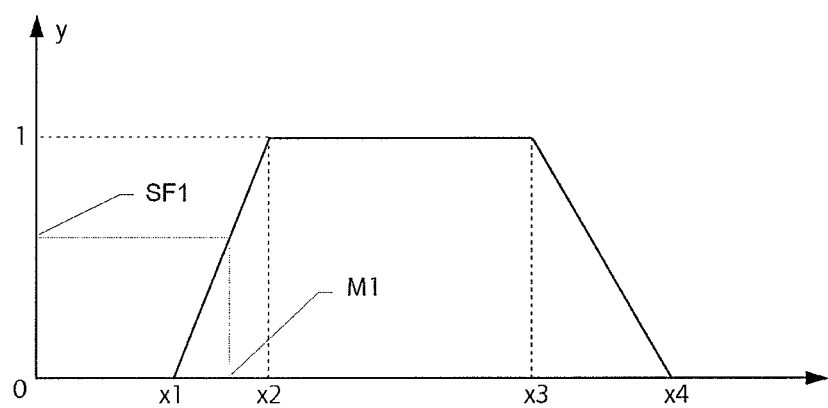
FIG. 10 illustrates a diagram schematically indicating the determination of a correlation factor in accordance with an embodiment of the present application.

FIG. 10 schematically indicates a trapeze method to determine a similarity factor of a certain key element. Threshold values x1, x2, x3, x4 are retrieved from a database and determine in what region the relative amount of a certain key element may vary. Between the inner threshold values x2, x3 the similarity factor is set to 1. Between the outer threshold values x1, x4 and the neighbouring inner threshold value x2, x3 the similarity factor increases, respectively decreases in the shown example in a linear manner. A certain measured value M1 e.g. determined by a spectrometer results in a similarity factor SF1 for a specific key element. Depending on the field of application other non-linear interpolation algorithms may be appropriate. The threshold values are e.g. retrieved from engineering standards or other specifications. Instead of the described trapeze method it may be foreseen that a user can apply his own calculation method to determine the similarity factor.

The system and method of the present invention may be implemented and run on a general-purpose computer, if desired.

Although the present invention has been described in relation to particular embodiments thereof, many other variations and modifications and other uses will become apparent to those skilled in the art. It is preferred, therefore, that the present invention be limited not by the specific disclosure herein.

What is claimed is:

1. A data processing system to identify an unknown metal alloy comprising:
   a. a display and an operating system, wherein the operating system is operable to perform method steps comprising:
   b. receiving a chemical composition of the metal alloy, the chemical composition including key elements and trap elements;
   c. determining key elements of the metal alloy based on information retrieved from a database, a key element being indicative of an alloy composition and a trap element being non-indicative of an alloy composition;
   d. comparing a relative amount of each key element present with a threshold value amount of each key element, the threshold value amount is retrieved from a dataset of a specific known metal alloy in the database;
   e. determining a similarity factor between the relative amount of each key element and the threshold value amount of each key element;
   f. calculating a correlation factor based on the similarity factor for each key element; and
   g. providing a result list of metal alloys, retrieved from the database including metal alloys with respective chemical compositions similar to that of the determined chemical composition based on the correlation factors, wherein the respective chemical compositions of the metal alloys listed in the result list match the determined chemical composition; and
   h. applying a weighting factor to at least one specific key element in the calculation of the correlation factor based on the classification of the metal alloys.

2. The data processing system of claim 1, wherein a coarse classification of the metal alloy is made manually or automatically based on the metal alloy's nature prior to determining the key elements and trap elements.

3. The data processing system of claim 1, wherein the method steps are repeated several times for different groups of metals and results for the different groups are compared with each other.

4. The data processing system of claim 1, wherein key elements and trap elements are determined based on a classification of known metal alloys.

5. The data processing system of claim 1, wherein the similarity factor ranges between 0 and 1.

6. The data processing system of claim 1, wherein the similarity factor is determined by a trapez method.

7. The data processing system of claim 1, wherein the chemical composition is received from a spectrometer interconnected to a device which includes the operating system that performs the method steps.

8. The data processing system of claim 1, further comprising calculating a total similarity factor based on the similarity factor of the key elements in the chemical composition.

9. The data processing system of claim 1, wherein the correlation factor is calculated by a summation of the similarity factors.

* * * * *